United States Patent

Myers, Jr. et al.

[11] 4,152,360
[45] May 1, 1979

[54] PREPARATION OF TETRAMETHYLENE NORTRICYCLANE

[75] Inventors: Harry K. Myers, Jr., Aston; Abraham Schneider, Overbrook Hills, both of Pa.

[73] Assignee: Sun Oil Company, Philadelphia, Pa.

[21] Appl. No.: 819,443

[22] Filed: Jul. 27, 1977

[51] Int. Cl.² ............................................. C07C 13/28
[52] U.S. Cl. ............................... 585/361; 149/109.4; 149/109.6; 149/120; 585/14
[58] Field of Search .............. 260/666 PY; 149/109.4, 149/109.6

[56] References Cited

U.S. PATENT DOCUMENTS 2,875,256  2/1959  Hyman et al. ................. 260/666 A

OTHER PUBLICATIONS

Akio Takahashi et al., J. Chem. Soc. Sect. P Chem. Commun. No. 22, p. 1473, 1970.

A. Carbonaro et al., J. Org. Chem. vol. 36, No. 10, pp. 1443–1445, 1971.

*Primary Examiner*—Veronica O'Keefe
*Attorney, Agent, or Firm*—J. Edward Hess; Donald R. Johnson; Anthony Potts, Jr.

[57] ABSTRACT

Catalytic codimerization of norbornadiene and 1,3-butadiene, using a three-component homogeneous catalytic system consisting of cobaltic or cobaltous acetylacetonate, 1,2-bisdiphenylphosphino ethane and an alkyl aluminum chloride, yields a codimer having the following structure:

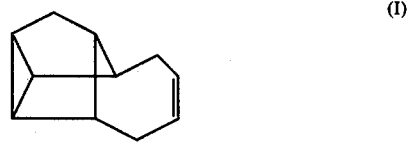

(I)

Upon hydrogenation, codimer I forms tetramethylene nortricyclane having utility as a high energy fuel.

10 Claims, No Drawings

PREPARATION OF TETRAMETHYLENE NORTRICYCLANE

BACKGROUND OF THE INVENTION

The invention herein described was made in the course of or under a contract thereunder with the United States Air Force Systems Command.

The invention relates to the catalytic codimerization of norbornadiene and 1,3-butadiene. Particularly the invention relates to the preparation of an olefinic codimer of norbornadiene and 1,3-butadiene using a specified catalyst system. Hydrogenation of the olefinic codimer yields a saturated codimer having utility as a high energy fuel or a diluent for such fuels.

High energy fuel, which is often referred to as a high density fuel, can be used in either jet or rocket propulsion. Jet propulsion includes a jet engine which can be used for a missile plane and others and includes the three basic types, i.e., ramjet, turbo-jet and pulse jet. The term rocket generally refers to a device containing its own oxygen or oxidizing agent.

Norbornadiene is also known as bicyclo-(2.2.1) heptadiene-2,5. A method of preparation is disclosed in U.S. Pat. No. 2,875,256 issued Feb. 24, 1959. Hereinafter, norbornadiene is referred to as NBD. The latter can be represented by either one of the following structural formulas:

 OR 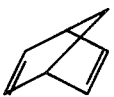

NBD can be easily dimerized to an exo-exo hexacyclic dimer. Thus one problem in reacting NBD with another hydrocarbon reactant is to minimize the formation of the foregoing dimer while encouraging the formation of the desired codimer.

Codimerization of NBD and 1,3-butadiene, hereinafter referred to as BD. using a catalyst system consisting of tris (acetylacetonate) iron-aluminum diethyl chloride-bis (diphenylphosphine) ethane yields codimer I according to A. Greco, et al, Journal of Organic Chemistry, Vol. 35, No. 1, Jan. 1970, page 271, which has the following structure:

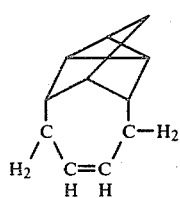 OR 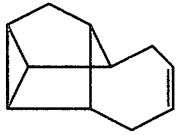

(I)                 (I)

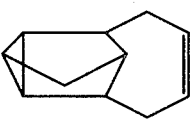

(I)

The codimer I was prepared with a yield of about 40 mole%. Also, Carbonaro et al, in Journal of Organic Chemistry, Vol. 36, No. 10, 1971, page 1443 uses cobaltous chloride, triethyl aluminum or diethyl aluminum chloride, and bis(diphenylphosphine) ethane. Codimer I was prepared with a yield of about 40–68 mole % depending the particular alkyl aluminum chloride.

Codimerization of NBD and BD using cobaltic acetylacetonate, hereinafter referred to as $CoA_3$, and triethylaluminum yields, in addition to a minor amount of codimer I, a major amount of related 5-butadienyl nrborn-2-ene, II, according to A. Takahashi, et al, the Journal of the Chemical Society, No. 22, 1970, page 1473. The following is the structure of codimer II:

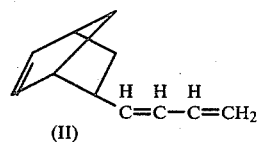

(II)

Cobaltous acetylacetonate is referred to hereinafter as $CoA_2$. Both acetylacetonates will be referred to collectively as CoA.

Thus, the aforementioned work indicates that the specific synthesis problem is to obtain codimer I in both excellent conversion and selectivity and with a rapid reaction rate.

SUMMARY OF THE INVENTION

Rapid codimerization of NBD and BD is obtained using a catalytic amount of a three-component homogeneous catalytic system consisting of $CoA_3$ or $CoA_2$, 1,2-bisdiphenylphosphino ethane, hereinafter referred to as DIPHOS, and an alkyl aluminum chloride, hereinafter referred to as AAC. Both the yield and selectivity, as to the codimer I, are excellent and the reaction rate is rapid. Resulting codimer can be hydrogenated and then used as high energy fuel.

DESCRIPTION

The catalytic codimerization of NBD and BD via present invention can be represented by the following formula reaction:

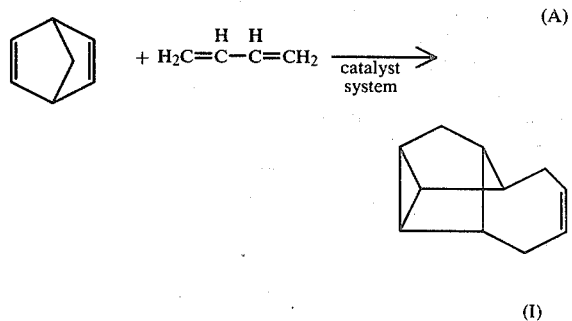

(A)

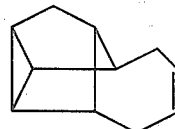

(I)

As shown NBD and BD are contacted in the presence of a catalytic amount of the catalyst system which is defined herein.

Olefinic codimer I is a tetracyclic hydrocarbon having the molecular formula $C_{11}H_{14}$ and a C/H molar ratio of 0.786. Codimer I, prepared as described hereinafter, with a purity of 99%, has a boiling point of 66°–67° C. at 0.8 mm Hg; a melting point of less than 0° C.; a net heating value of greater than 150,000 BTU/gallon; a density at d20/4 of greater than 0.98; and a KV at 100° F. of about 4.0 cs.

Codimer I upon hydrogenation forms tetramethylene nortricyclane III in a major amount. This material is a tetracyclic hydrocarbon having the molecular formula $C_{11}H_{16}$ and a C/H ratio of 0.688. The hydrogenation of olefinic codimer I can be represented by the following formula reaction:

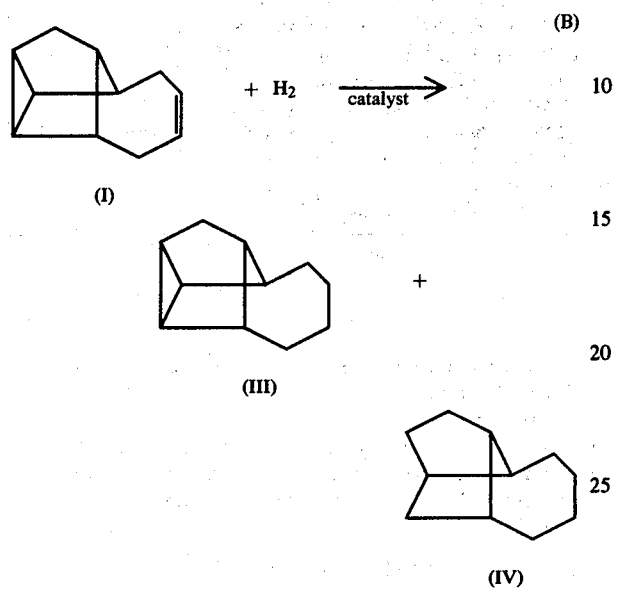

(B)

The relative amounts of codimer III and IV can be varied substantially by changes in operating conditions. Codimer III, prepared as described hereinafter, at 99% purity, has a boiling point of 33°-36° C. at 0.15mm Hg; a net heating value of 150,343 BTU/gal; a density at d20/4 of 0.9853; and a KV at 100° F. of 4.14 cs. This codimer is a clear colorless liquid and has a melting point of approximately −6° C. as determined by differential scanning calorimetry.

The NBD used can contain a nominal amount of similar hydrocarbons, however, which if present should not be of a type which could adversely effect the reaction. If the NBD used contains undesirable hydrocarbons, the latter can be removed by known means. The foregoing also applies to the BD used. Thus the hydrocarbons used in the invention can consist essentially of NBD and BD.

In the codimerization of NBD and BD one mole of each reacts with the other to form one mole of the NBD-BD codimer I. However, if the NBD to BD mole ratio is too large NBD homodimerization can occur with an adverse effect on codimer yields. On the other hand, if the NBD to BD mole ratio is too low then the yield per pass can be too low and hence uneconomical. Within the aforementioned limits a preferred NBD to BD mole ratio is in the range between from about 0.01 to about 10 with about 0.1 to about 5 more preferred.

The catalytic system favoring the aforementioned codimerization reaction (A) contains three components. All three components of the catalyst system are commercially available and methods for their preparation are known. The three are $CoA_3$ or $CoA_2$, DIPHOS and AAC. The AAC can be selected from the group consisting of diethylaluminum chloride, ethyl aluminum dichloride and ethyl aluminum sesquichloride. The latter three are referred to as DEAC, EADC and EASC, respectively. The amount of any component present is a catalytic amount so that a suitable conversion to codimer I occurs and the selectivity as to it is sufficient. Material, which during the codimerization reaction could adversely affect the catalyst system, should not be present. For example, the presence of hydroxylic compounds such as water, alcohol or oxygen from air could deactivate the catalyst system.

The amount of CoA present should be catalytically sufficient to obtain the desired product. Generally the NBD to CoA mole ratio can range between from about 10 to about 2000 with a preferred range between from about 20 to about 1000.

The second component of the catalyst system is DIPHOS which has the following formula: $[(C_6H_5)_2PCH_2]_2$. The amount of this second component of the catalyst system should be catalytically sufficient to obtain the desired product. Generally the DIPHOS to CoA mole ratio can range between from about 0.1 to about 5 with a preferred range between from about 0.25 to about 4.

DEAC, EADC or EASC is the third component of the catalyst system with DEAC preferred. The amount of the third component can vary substantially but generally it relates to the amount of CoA used. An effective DEAC, EADC or EASC to CoA mole ratio can be between from about 1 to about 100 with from about 3 to about 50 preferred and from about 5 to about 20 more preferred. Generally, when DEAC, EADC or EASC is used it is advantageous to conduct the reaction under substantially anhydrous conditions and under an inert gas blanket. Excess DEAC, EADC or EASC also serves as a scavenger.

Selectivity refers to the amount, mole or weight, of a particular compound formed divided by the amount of all compounds formed. From a commercial standpoint the economics of an overall process determines the optimal levels for both the selectivity and yield.

The reaction time required for an economically satisfactory selectivity and/or yield depends on a number of factors, such as catalyst to feed ratio, as well as operating conditions. Also the economics depend on capital investment versus conversion per pass and the like. The catalyst is feed ratios are discussed herein while typical conditions are provided by the Example.

A solvent can be used in the codimerization reaction. The solvent can be inert or it can be the NBD itself. Since the reaction is mildly exothermic the solvent can serve as a heat sink. It can also assist in solubilizing the reaction components, that is the feed and the components of the catalyst, and thereby provide for a homogeneous reaction medium. Some solvent can be added to the system as a carrier for one or more of the catalyst components. For example, DEAC is often maintained in an inert solvent such as toluene rather than NBD itself. Furthermore, the solvent should not adversely react with the feed, products or catalyst, therefore, if it is not NBD, it should be inert. Also, presence of the solvent can facilitate the handling of the reaction mixture. Classes of suitable inert solvents include aromatic hydrocarbons, cycloparaffins, cycloolefins, ethers, halogenated aromatics, halogenated paraffins and halogenated cycloparaffins. Specific examples include benzene, toluene, xylenes, cyclohexane, cyclopentene, diethylether, chlorobenzene, bromobenzene, chlorinated cyclohexane and the like. As to the amount of solvent used, excessive amounts decrease the reaction rate, and thus adversely affect the economics for a commercial operation. All three components are commercially available and methods for their preparation are well known.

The codimerization of NBD and BD with the three-component catalyst system can occur at ambient temperature. Thus the temperature of the homogeneous feed catalyst system mixture need not be raised to initiate reaction A. Of course, if the mixture is at an extremely low temperature, then heating of the cooled mixture could be necessary. However, once reaction A is underway, some heat is generated and the temperature of the mixture increases. If the temperature increases too much then some cooling would be required. Generally, however, the codimerization of NBD and BD with a reasonable amount of the three-component catalyst system is not characterized by an extremely rapid exotherm.

Selective codimerization of the NBD and BD most efficiently occurs in a liquid or a gaseous-liquid phase and therefore it is not desirable to have the reaction temperature largely exceed the boiling points of the NBD and/or any solvent. Conversely, if the temperature is too low the reaction rate will be too slow to be economically feasible. An operable temperature range is between from about 20° C. to about 100° C. with about 25° C. to about 85° C. a preferred range. The operating pressure can vary substantially, however, it can range from about atmospheric up to about 2000 psi with about 1000 psi a preferred upper value. Process economics favor lower operating pressure, however, a moderately elevated reaction pressure may be desirable to keep the BD in solution.

To further illustrate the invention, the following examples and comparisons are provided.

EXAMPLES

The accompanying Table summarizes the codimerization runs and a comparative homodimerization run which were performed. Runs 1, 2, 3 were screening runs carried out in test tubes and the results are of a qualitative nature. In run 1, no BD was present; the data indicates that, at the conditions stated, the NBD by itself dimerizes into Binor-S and hexacyclics. Runs 2 and 3 indicate that the presence of BD cause codimer I to be formed. Run 3 was different from the other runs in that the DIPHOS was withheld initially and that when no reaction seemed to be taking place it was added. Runs 4 and 5 were carried out under more carefully controlled conditions; comparison of the latter two indicate that the NBD/BD mole ratio can influence the yield and selectivity of the codimer I.

In run 4, 0.712 gram (2 millimoles) of $CoA_3$, i.e., (Co$(C_5H_7O_2)_3$), 1.194 grams (3 millimoles) of DIPHOS, 25 milliliters of toluene and 5 milliliters (49.3 millimoles) of NBD (all of which were at 24° C.) were added to a Fisher-Porter reaction vessel. The resulting mixture was stirred, deaerated with argon and cooled to $-10°$ C. Into a second Fisher-Porter reaction vessel were added 5 milliliters of toluene and 95 milliliters (937.3 millimoles) of NBD, which were at 24° C., and the resulting mixture was deaerated. Then 8.88 grams (164 millimoles) of BD were added to the second vessel and the resulting mixture stirred.

After the preparation of the mixtures in both vessels 25 millimoles of DEAC, in toluene, were added to the first vessel and the contents of this vessel were warmed to 43° C. with stirring. Then the contents of the second vessel were slowly pumped into the first vessel and the reaction mixture was stirred for 180 minutes. The reaction was exothermic and the maximum reaction temperature during the 180 minutes was 83° C.

At the conclusion of the reaction period the reaction mixture was treated with aqueous HCl at 0° C. to quench the catalyst. Some of the hydrocarbon material was separated from the quenched liquid and analyzed by vapor phase chromatographic analysis (vpc). It showed that the butadiene had been quantitatively consumed and that approximately 30% by weight of the NBD had reacted. According to the analysis two major reaction products were formed: the NBD-BD codimer I with 59.5% selectivity and an exo-exo hexacyclichomodimer with 40% selectivity.

In Run 5, some 0.712 grams (2 millimoles) of $CoA_3$, 1.194 grams (3 millimoles) of DIPHOS, 35 milliliters of toluene and 2 milliliters of NBD, which were at 24° C., were added to a Fisher-Porter reaction vessel. The resulting mixture was stirred, deaerated with argon and cooled to $-20°$ C. Also into a second Fisher-Porter reaction vessel were added 23 milliliters (226.9 millimoles) of deaerated NBD and 30 milliliters (344 millimoles) of BD. The resulting mixture was warmed to 24° C.

After the preparation of the mixtures in both vessels 20 millimoles of DEAC, in toluene, were added to the first vessel and its contents warmed to 50° C. After cooling the first vessel to 40° C. the contents of the second vessel were slowly pumped into the first vessel and the reaction mixture was stirred for 197 minutes. The reaction was exothermic and the maximum reaction temperature during the 197 minutes was 50° C.

At the conclusion of the reaction period the reaction mixture was treated with aqueous HCl at 0° C. to quench the catalyst. Some of the hydrocarbon material was separated from the quenched liquid and analyzed by vpc. It showed that the reaction was nearly completed; that little or no homodimerization of NBD had occurred; and that the NBD-BD codimer had been formed at about a 92% selectivity with a 97% yield of dimers.

Separated hydrocarbon material from run 5 was distilled and the portion boiling at 66°–67° C. at 0.8mm Hg was collected. The collected material was approximately 99% pure codimer as determined by vpc.

Some of the 99% pure NBD-BD codimer I was hydrogenated using platinum oxide as the catalyst at 25° C. and 5 psi hydrogen in a glass Parr hydrogenation apparatus. The resulting product was analyzed by vpc and found to contain 13% of compound IV and 85% of the tetramethylenenorticyclane III. Infrared spectrum and NMR spectrum of codimers I and III were consistent with the assigned structure.

Runs 4 and 5 were liquid reactions compared to run 2 in which gaseous BD was bubbled through a solution consisting of NBD and the catalytic system. In the runs 4 and 5 the BD reacted at a rapid rate so that the pressure buildup was relatively low compared to the vapor pressure of BD at the reaction temperature.

A run was made using $CoA_2((Co(C_5H_7O_2)_2)$ in lieu of $CoA_3$. In this run 0.04 millimoles of $CoA_2$, 0.06 millimoles of DIPHOS, and 9.8 millimoles of NBD were mixed at a temperature of 24° C. To completely dissolve the $CoA_2$ the mixture was warmed to about 55° C. and then cooled to 24° C. Then BD was slowly bubbled through the mixture while it was warmed to 53° C. and then 0.4 millimoles of DEAC was added. The BD was bubbled through the mixture for 110 minutes. The mixture was maintained at the temperature of 53° C. for an additional 145 minutes at which time a sample was taken, the catalyst killed, and the hydrocarbon analyzed by vpc. The yields and selectives were as follows: NBD conversion was 28.5%, and selectivity to codimer was 91.2%; NBD yield to codimer was 26.1%.

Analogous results will be obtained at different catalyst ratios and feed ratios.

Another run was made to determine if excess DIPHOS interfered with the codimerization. In this run 0.04 millimoles of $CoA_3$, 0.2 millimoles of DIPHOS and 9.8 millimoles of NBD were mixed at a temperature of 24° C. (The ratio of DIPHOS to $CoA_3$ was 5). Then BD was slowly bubbled through the mixture while it was warmed to 53° C. and then 0.4 milliliters of DEAC were added. The BD was bubbled through for 290 minutes, while the temperature was maintained at 49° C., at which time a sample was taken, the catalyst killed and the hydrocarbon analyzed by vpc. The conversion was extremely low, if any, did in fact occur.

A comparative run using nickel acetylacetonate, triphenylphosphine and DEAC using a high mole ratio of NBD/BD for 15 hours with a maximum temperature of 60° C. resulted in a very low yield of dimer and no codimer I. Also a comparative run was made using $CoA_3$ and DEAC but not DIPHOS. With the aforementioned two-component catalyst system conversion was extremely low, if any, did in fact occur.

TABLE

| | | | CODIMERIZATION OF NBD AND BD | | | | | | | | |
|---|---|---|---|---|---|---|---|---|---|---|---|
| | Mole Ratio of | | | Max. | | | Yield | Selectivity % | | | |
| Run | NBD/BD | NBD/$CoA_3$ | DEAC/$CoA_3$ | DIPHOS/$CoA_3$ | Max. Pressure, psig | Max. Temp.—°C. | Time Hours | to Dimer % | Codi- imer I | Penta- Cyclics | Hexa- Cyclics | Bin- or-S |
| 1 | 0 | 493 | 20 | 1 - 1.5 | — | 60 | 15 | 38 | 0 | — | 37 | 62 |
| 2 | High$^a$ | 987 | 20 | 1 - 1.5 | — | 75 | 15 | 52 | 38 | — | 25 | 34 |
| 3 | 4.0 | 493 | 37 | 1 - 1.5$^b$ | — | 60 | 15 | 38 | 57 | 11 | 18 | 5 |
| 4 | 6.0 | 493.5 | 12.5 | 1.5 | 33 | 83 | 3.0 | 30 | 59 | — | 41 | 0 |
| 5 | 0.72 | 123.5 | 10 | 1.5 | 20 | 50 | 3.2 | 97 | 92 | — | — | — |

Notes:
$^a$BD bubbled through solution
$^b$Initially DIPHOS was not added

The invention claimed is:

1. Process for the catalytic codimerization of norbornadiene and 1,3-butadiene comprising:
   (a) contacting norbornadiene and 1,3-butadiene in the presence of a catalytic amount of a three-component homogeneous catalytic system consisting of cobaltic or cobaltous acetylacetonate, 1,2-bisdiphenylphosphino ethane and one of the following alkyl aluminum chlorides: diethyaluminum chloride, ethyl aluminum, dichloride, and ethyl aluminum sesquichloride;
   (b) having the contacting occurring at a temperature within the range from between about 20° C. to about 100° C.; and
   (c) continuing the contacting until the norbornadiene and 1,3-butadiene codimer is prepared.

2. Process according to claim 1 wherein the norbornadiene to cobaltic acetylacetonate mole ratio is in the range between from about 10 to about 2000.

3. Process according to claim 1 wherein the bisdiphenylphosphino ethane to the acetylacetonate mole ratio is in the range between from about 0.1 to about 5.

4. Process according to claim 1 wherein the norbornadiene to 1,3-butadiene mole ratio is in the range between from about 0.01 to about 10.

5. Process according to claim 1 wherein the alkyl aluminum chloride to the acetylacetonate mole ratio is in the range between from about 1 to about 100.

6. Process according to claim 1 wherein an inert solvent is present.

7. Process according to claim 6 wherein the inert solvent is selected from the group consisting of aromatic hydrocarbon, cycloparaffin, cycloolefin, ether, halogenated aromatic hydrocarbon, halogenated paraffin and halogenated cycloparaffin.

8. Process according to claim 7 wherein the norbornadiene to cobaltic acetylacetonate mole ratio is in the range between from about 10 to about 2000.

9. Process according to claim 8 wherein the bisdiphenylphosphino ethane to the acetylacetonate mole is in the range between from about 0.1 to about 5.

10. Process according to claim 9 wherein the norbornadiene to 1,3-butadiene mole ratio is in the range between from about 0.01 to about 10 and the alkyl aluminum chloride to the acetylacetonate mole ratio is in the range between from about 1 to about 100.

* * * * *

UNITED STATES PATENT OFFICE
CERTIFICATE OF CORRECTION

PATENT NO. : 4,152,360
DATED : May 1, 1979
INVENTOR(S) : HARRY K. MYERS, JR. & ABRAHAM SCHNEIDER

It is certified that error appears in the above-identified patent and that said Letters Patent are hereby corrected as shown below:

Assignee: SUN OIL COMPANY OF PENNSYLVANIA, Philadelphia, PA.

Signed and Sealed this

Seventeenth Day of July 1979

[SEAL]

*Attest:*

LUTRELLE F. PARKER
*Acting Commissioner of Patents and Trademarks*

*Attesting Officer*